US006837956B2

(12) United States Patent
Cowell et al.

(10) Patent No.: US 6,837,956 B2
(45) Date of Patent: Jan. 4, 2005

(54) SYSTEM FOR APERTURING AND COAPERTURING WEBS AND WEB ASSEMBLIES

(75) Inventors: Christine M. Cowell, Fond du Lac, WI (US); Richard W. Kubalek, Appleton, WI (US); Andrew M. Lake, Manitowoc, WI (US); Jeffrey D. Lindsay, Appleton, WI (US); Susan J. Moder, Appleton, WI (US); Shelley R. Rasmussen, Oshkosh, WI (US); Laura J. Walker, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 241 days.

(21) Appl. No.: 10/306,550

(22) Filed: Nov. 26, 2002

(65) Prior Publication Data

US 2003/0121380 A1 Jul. 3, 2003

Related U.S. Application Data (60) Provisional application No. 60/336,096, filed on Nov. 30, 2001.

(51) Int. Cl.[7] .............................................. B32B 31/00
(52) U.S. Cl. ...................... 156/252; 156/265; 156/513; 156/519
(58) Field of Search ................................ 156/250, 252, 156/256, 264, 265, 510, 513, 516, 517, 519, 555, 582

(56) References Cited

U.S. PATENT DOCUMENTS

| | | |
|---|---|---|
| 3,585,104 A | 6/1971 | Kleinert |
| 4,234,775 A | 11/1980 | Wolfberg et al. |
| 4,440,597 A | 4/1984 | Wells et al. |
| 4,514,345 A | 4/1985 | Johnson et al. |
| 4,528,239 A | 7/1985 | Trokhan |
| 4,529,480 A | 7/1985 | Trokhan |
| 4,556,450 A | 12/1985 | Chuang et al. |
| 4,594,130 A | 6/1986 | Chang et al. |
| 4,793,898 A | 12/1988 | Laamanen et al. |
| 4,820,294 A | 4/1989 | Morris |
| 4,886,632 A | 12/1989 | Van Iten et al. |
| 4,988,344 A | 1/1991 | Reising et al. |
| 4,988,345 A | 1/1991 | Reising |
| 5,098,522 A | 3/1992 | Smurkoski et al. |
| 5,169,571 A | 12/1992 | Buckley |
| 5,171,238 A | 12/1992 | Kajander |
| 5,178,729 A | 1/1993 | Janda |
| 5,188,625 A | 2/1993 | Van Iten et al. |
| 5,228,947 A | 7/1993 | Churchland |
| 5,230,776 A | 7/1993 | Andersson et al. |

(List continued on next page.)

FOREIGN PATENT DOCUMENTS

| | | |
|---|---|---|
| EP | 0 343 940 B2 | 11/1999 |
| WO | WO 96/39109 A1 | 12/1996 |
| WO | WO 99/22686 A1 | 5/1999 |

(List continued on next page.)

OTHER PUBLICATIONS

Foulger, M. and J. Parisian, "New Developments in Hot Pressing," Pulp & Paper Canada, vol. 101, No. 2, 2000, pp. 47–49.

(List continued on next page.)

*Primary Examiner*—James Sells (57) ABSTRACT

Improved aperturing of a web can be obtained by providing pins with an extended tapered section that is substantially convex in shape. When the tapered section is longer than the penetration depth of the pins into the receiving recesses of a female roll, frictional forces in the nip between layers are reduced. Pins with extended tapered sections can be used in devices for producing apertured composite web assemblies comprising sections of absorbent matter attached to a nonwoven web or other carrier layer.

26 Claims, 6 Drawing Sheets

U.S. PATENT DOCUMENTS

| | | |
|---|---|---|
| 5,260,171 A | 11/1993 | Smurkoski et al. |
| 5,275,700 A | 1/1994 | Trokhan |
| 5,328,565 A | 7/1994 | Rasch et al. |
| 5,334,289 A | 8/1994 | Trokhan et al. |
| 5,338,169 A | 8/1994 | Buckley |
| 5,353,521 A | 10/1994 | Orloff |
| 5,431,786 A | 7/1995 | Rasch et al. |
| 5,437,653 A | 8/1995 | Gilman et al. |
| 5,470,326 A | 11/1995 | Dabi et al. |
| 5,494,554 A | 2/1996 | Edwards et al. |
| 5,496,624 A | 3/1996 | Stelljes, Jr. et al. |
| 5,500,277 A | 3/1996 | Trakhan et al. |
| 5,514,523 A | 5/1996 | Trokhan et al. |
| 5,536,921 A | 7/1996 | Hedrick et al. |
| 5,554,467 A | 9/1996 | Trokhan et al. |
| 5,566,724 A | 10/1996 | Trokhan et al. |
| 5,573,719 A | 11/1996 | Fitting |
| 5,595,628 A | 1/1997 | Gordon et al. |
| 5,598,642 A | 2/1997 | Orloff et al. |
| 5,598,643 A | 2/1997 | Chuang et al. |
| 5,624,790 A | 4/1997 | Trokhan et al. |
| 5,628,876 A | 5/1997 | Ayers et al. |
| 5,637,194 A | 6/1997 | Ampulski et al. |
| 5,656,132 A | 8/1997 | Farrington, Jr. et al. |
| 5,772,845 A | 6/1998 | Farrington, Jr. et al. |
| 5,855,739 A | 1/1999 | Ampulski et al. |
| 5,897,745 A | 4/1999 | Ampulski et al. |
| 5,916,203 A | 6/1999 | Brandon et al. |
| 5,948,507 A | 9/1999 | Chen et al. |
| 5,958,275 A | 9/1999 | Joines et al. |
| 5,962,112 A | 10/1999 | Haynes et al. |
| 5,986,167 A | 11/1999 | Arteman et al. |
| 5,990,377 A | 11/1999 | Chen et al. |
| 6,010,598 A | 1/2000 | Boutilier et al. |
| 6,020,580 A | 2/2000 | Lewis et al. |
| 6,096,169 A | 8/2000 | Hermans et al. |
| 6,103,060 A | 8/2000 | Munerelle et al. |
| 6,103,063 A | 8/2000 | Oriaran et al. |
| 6,143,135 A | 11/2000 | Hada et al. |
| 6,217,691 B1 * | 4/2001 | Vair et al. .................. 156/176 |
| 6,270,608 B1 * | 8/2001 | Vair et al. .................. 156/176 |
| 6,306,234 B1 | 10/2001 | Barker et al. |
| 6,443,938 B1 | 9/2002 | Vogt |

FOREIGN PATENT DOCUMENTS

| | | |
|---|---|---|
| WO | WO 99/25550 A1 | 5/1999 |
| WO | WO 00/59430 A1 | 10/2000 |
| WO | WO 00/59431 A1 | 10/2000 |
| WO | WO 00/74620 A1 | 12/2000 |
| WO | WO 01/17475 A1 | 3/2001 |
| WO | WO 01/26592 A1 | 4/2001 |
| WO | WO 01/26595 A1 | 4/2001 |
| WO | WO 01/72251 A1 | 10/2001 |
| WO | WO 02/41815 A1 | 5/2002 |

OTHER PUBLICATIONS

James, Rhiannon, Squeezing More Out of Pressing and Drying, Pulp and Paper International, vol. 41, No. 12, Dec. 1999, pp. 13–17.

Lindsay, Jeffrey D., "Displacement Dewatering To Maintain Bulk," Paperi Ja Puu—Paper And Timber, vol. 74, No. 3, 1992, pp. 232–242.

Metaxas, A.C. and R.J. Meredith, Industrial Microwave Heating, Peter Peregrinus Ltd., London, 1983, pp. 183–195.

Federal Specification UU–T–595b, "Towel, Wiping, Paper: Industrial And Institutional," Apr. 4, 1967, 8 pages.

Federal Specification UU–T–595c, "Towel, Wiping, Paper: Industrial And Institutional," Jul. 27, 1976, 8 pages.

* cited by examiner

Prior Art

FIGURE 5

SYSTEM FOR APERTURING AND COAPERTURING WEBS AND WEB ASSEMBLIES

This application claims priority from U.S. Provisional Application No. 60/336,096 filed Nov. 30, 2001.

BACKGROUND

In the production of disposable absorbent articles, pin aperturing is a widely used and inexpensive method for providing apertures in a web for purposes such as enhancing fluid transport, increasing void space, or improving the appearance of a product. Both single webs and composite webs can be pin apertured in an aperturing nip comprising a pin roll and a female roll. When an assembly of two or more layers are apertured simultaneously, the assembly is said to be coapertured. Aperturing and coaperturing can be desirable for many products, but they pose a number of challenges for high-speed manufacturing. Challenges arise in many cases due to in-plane deformation of the web or web assembly as it passes through an aperturing nip. As a pin first engages the web, the tip of the pin travels at a higher radial velocity than the perimeter of the opposing female roll, resulting in shear of the web near the tip of the pin. As the pin pushes the web down into the receiving recess of the female roll, more in-plane dislocation of the web occurs. The shear or dislocation experienced by portions of the web near the resulting apertures can reduce the clarity of the aperture. When the web has been previously embossed or otherwise textured, the clarity of the embossment or texture can suffer because of in-plane dislocation and shear of the web.

Figure 5:
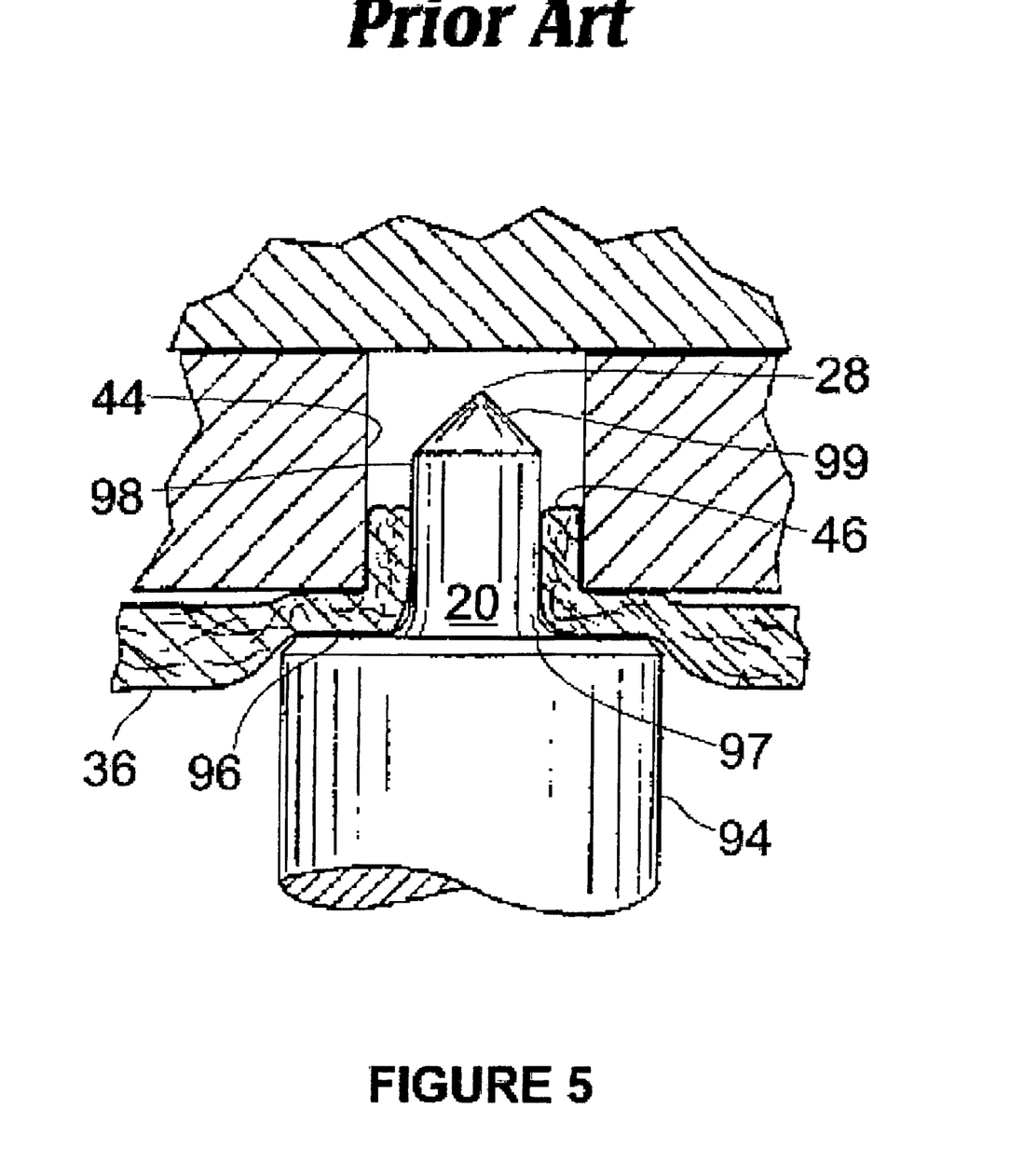
FIG. 5 shows a prior art pin.

Examples of prior pin designs for aperturing webs are disclosed in U.S. Pat. No. 5,986,167, "Method of Distributing Liquid in Apertured Absorbent Pads," issued Nov. 16, 1999 to Arteman and Myers; and U.S. Pat. No. 4,886,632, "Method of Perforating a Nonwoven Web and Use of the Web as a Cover for a Feminine Pad," issued Dec. 12, 1989 to Van Iten et al., both of which are herein incorporated by reference. An exemplary pin design from the Van Iten patent is shown in FIG. 5, discussed hereafter Particularly severe challenges are encountered in coaperturing web assemblies comprising two or more layers such as a high-bulk absorbent web of fluff disposed on a denser or substantially thinner nonwoven web or film. The dissimilar physical properties of the two or more layers can result in complex in-plane stresses and a variety of aperture defects or web deformation problems.

Designs for aperturing pins usually seek to minimize pin length because longer pins create a higher level of differential movement in the aperturing nip, cause more in-plane dislocation of the web, and are more likely to become jammed in the receiving recesses of the female roll. Nevertheless, conventional pin designs result in a variety of problems with aperture quality. It is believed that one problem with prior pin design has been the abbreviated length of the tapered section, which is often tapered at a high angle relative to the vertical axis, such as a 45 degree angle. The short span of the tapered section tends to result in greater web disruption and densification of the web near the aperture.

What is needed is an improved aperturing method wherein the in-plane dislocations are minimized, and specifically wherein the amount of material pushed into the receiving recesses of the female roll is minimized. Achieving this result requires consideration of the shape and length of the pins, the geometry of the receiving recesses of the female roll, and the properties of the web.

SUMMARY

It has been discovered that decreased in-plane deformation of a web (including a composite web assembly) by aperturing pins can be achieved during aperturing if the pins are provided with a tapered section of sufficient length to reduce frictional forces between the pins and the web in the aperturing nip to reduce the amount of material dragged by the pins into the receiving recesses of the female roll, and to reduce friction between the pins and the web as the pins are withdrawn from the web. Achieving this objective is possible when the characteristic pin has a tapered section that not only extends into the receiving recess of the female roll, but also occupies a substantial portion of the gap between the pin roll and the female roll (i.e., between the support surface of the pin roll and the perimeter of the female roll) at mid-nip, such as at least about 10% of the gap, specifically at least about 30%, more specifically at least about 50%, more specifically still at least about 70%, and most specifically substantially all of the gap at mid-nip. The extended tapered section of the pin can reduce friction between the pin and the web as a substantial portion of the web remains in contact with the tapered portion as it is apertured. In one embodiment, the tapered section of the pin extending between the perimeter of the female roll at mid nip toward the pin roll is at least 30% as long as or longer than the thickness of the web in the aperturing nip, and more specifically at least 50% as long as the thickness of the web at mid-nip.

It has further been discovered that improved aperturing can be obtained by providing a non-conventional taper to the pin. Rather than the short linear or concave tapered shapes known in the art, a substantially convex tapered section can improve definition of the aperture in a high bulk absorbent web or composite web assembly. In a typical receiving recess of a female roll, the portions of the web or composite web assembly adjacent the aperture will be relatively more compressed and densified in the receiving recess by a pin with a convex taper than by a similar pin with a concave or linear taper, because in the vicinity of the aperture, a relatively greater portion of the diameter of the receiving recess will be occupied by the pin, resulting in higher compression of the web immediately adjacent to the aperture, and thus better definition of the aperture and preservation of the shape of the aperture. The definition of the aperture can be further improved when the receiving recess of the female roll is not simply a linear bore, as is conventional, but has a concave section adapted to cooperate with the tapered section of the pin and to densify the web between the tapered section of the pin and the concave section of the receiving recess.

In a useful process employing the highly tapered pins of the present invention, a composite web is formed by cutting absorbent sections from a web of fluff pulp (also known as airfelt) comprising a mat of comminuted wood pulp fibers, and placing the absorbent sections on a carrier layer that can be a porous nonwoven web such as a spunbond web that may serve as a cover layer in the completed absorbent article. Adhesive is placed on portions of the carrier layer to restrain the absorbent sections on the nonwoven web. The composite web assembly comprising absorbent sections on the carrier layer then enters an aperturing nip where tapered pins on a pin roll first contact the carrier layer and then puncture the carrier layer and the absorbent sections, thereby coaperturing the composite web assembly. The tapered section of the pins at mid-nip can extend from the tip of the pin in the receiving recess of the female roll into the gap between the female roll and pin roll, thereby reducing friction between the web and the pin during withdrawal of the pin from the web. A convexly tapered section of the pin coupled with a receiving recess having a concavely tapered portion can result in high definition of the apertured portion of the web.

The pins can be heated to fuse binder fibers in the absorbent web for improved definition of the aperture. The web exiting the aperturing nip can be wrapped for a distance against the female roll to improve the detachment of the web from the pin roll, particularly when the web is a composite web assembly having a nonwoven carrier layer on the side of the web toward the pin roll.

As used herein, "pin" refers to any protuberance rising from a support surface such as the surface of a roll or stamping plate which can be used to break through a web and form an aperture therein. A pin typically is a rigid material such as a metal, though composite materials and high-hardness plastics or ceramics can be used. A pin typically has a base that is held in place by the support surface, a shaft which rises above the support surface, and a tip distal from the base, which optionally but typically is tapered to form a sharp point. The base, shaft, and tip can all be formed from a cylindrical rod. Regarding the cross-section of the pin (i.e., the cross-section taken normal to the vertical axis of the pin and typically parallel to the portion of the support surface directly adjacent to the pin), any known shape can be used, though a circular cross-section is most typical. The cross-section of any portion of the pin can be substantially cylindrical, oval, rectangular, square, triangular, hexagonal, polygonal, and the like. It can be a rounded rectangle or other rounded polygon. The cross-section can be substantially convex or have concave elements. For example, it can be star-shaped or represent a circle with spaced apart notches (concave elements) therein, or can be a circle or other convex shape with ridges protruding outward. The base can have substantially the same cross-section as the shaft, or can be broader, notched, slotted, and the like to facilitate attachment into a the support surface.

The vertical profile of the mounted pin is the shape of the portion of the pin above the base as viewed in a cross-section taken through the vertical axis of the pin and normal to the support surface immediately adjacent the pin. Conventional pins often have a rectangular vertical profile (straight vertical sides) topped with a triangular portion where the tapered section has straight sides converging to a point.

Proper design of the shape of the pin and the corresponding receiving recesses of the female roll can be done using computer assisted design tools such as SurfaceWorks *** software. Two opposing solid rolls can be mechanically linked with a sliding link such that rotation of one roll causes the other roll to roll as well in the opposite direction. Proposed pin geometries (length, tapered section length, diameter), etc. coupled with roll geometry (diameter, gap between the opposing rolls) and receiving recess design can be modeled to ensure that a design is selected that prevent pins from colliding with the female roll and to ensure that the clearances between the pin and the receiving recess are adequate in the aperturing nip to compress the web around the aperture for good aperture definition.

In one embodiment, the stability of the web during aperturing is enhanced by providing a deformable restraint layer on the pin roll, such as a layer of a deformable foam material having holes to receive the pins. The deformable restraint layer on the pin roll can engage the web in the aperturing nip and reduce in-plane dislocation. The deformable layer can initially cover the pins or allow them to protrude only a short distance from the deformable layer, but in the nip as the deformable restraint layer presses against the web, the restraint layer can become compressed, causing it to recede and allowing the pins to emerge more fully to aperture the web. In this manner the web is restrained in the nip, reducing its tendency to shear or deform in the plane and reducing the tendency of the web to follow the pins as they enter into the receiving recesses of the female roll, leading to sharper aperture definition and improved runnability.

Though the use of a pin roll and opposing female roll is the most common method for high-speed, commercial aperturing of webs, it is recognized that other geometries can still be employed within the scope of the present invention. For example, tapered pins of the present invention and/or tapered receiving recesses according to the present invention can be employed in a planar geometry, in which the aperturing nip is defined by opposing plates such as a pin plate (in place of a pin roll) and a female plate (in place of a female roll). Operation of such a device requires repeated vertical motion of one or both plates to aperture the web as it travels between the opposing plates in the aperturing nip.

DETAILED DESCRIPTION OF PREFERRED EMBODIMENTS

FIGS. 1A–1D depict several embodiments in cross-sectional view of a pin 20 retained in a support 32 (e.g., a pin roll 50 or mounting plate) having a support surface 34. The pin 20 has a base 22, a shaft 24 rising above the support surface 34 of the support 32, a tapered section 26, and a tip 28 at the upper end of the tapered section 26. Distal to the tip 28 is the base end 30. The shaft 24 typically has a substantially uniform width, followed by the tapered section 26 whose width generally decreases with distance from the base end 30. In the tapered section 26, wherein the relationship between width and distance from the base end 30 is not linear in several embodiments. The sides of the tapered section 26 can be convex (as shown), concave, or a combination thereof, though in some embodiments a concave taper is particularly useful. The relationship between width and distance from the base end 30 is generally monotonic in preferred embodiments, but a short excursion from a monotonic decrease in width with distance from the base end 30 is not necessarily outside the scope of the present invention.

The shaft length S (the length of the shaft 24) can approach zero in embodiments in which the pin 20 begins tapering immediately above the support surface 34. The ratio of the shaft length S to the taper length T (the length of the tapered section 26) can be any of the following: 0 or greater, about 0.1 or greater, about 0.5 or greater, 1 or greater, 2 or greater, from about 0.1 to about 3, from about 0.2 to about 2, and from about 0.3 to about 1.5. The taper length T, by way of example, can be about 1 mm or greater; about 2 mm or greater, about 3 mm or greater, about 5 mm or greater, about 7 mm or greater, from about 1 mm to about 7 mm, and from about 2 mm to about 5 mm.

The overall length of the pin 20 is the extending length L of the pin 20 (the distance from the support surface 34 to the tip 28 of the pin) plus the base depth B of the pin 20 (the depth of the base 22 of the pin below the support surface 34). The pin 20 need not have a well defined base 22 set a finite depth B below the support surface 34, for the pin 20 can be unitary with the support 32 or with the pin roll itself 50, though for ease of manufacturing and repair, the pins 20 can be separate replaceable units embedded in a support 32.

The pin 20 extends into the receiving recess 44 of a female roll 42 by a penetration depth P, which can be selected based on the thickness and mechanical properties of the material to be apertured and the desired clarity or topography of the aperture or of the material adjacent to the aperture. For good definition of the aperture (i.e., good densification of the material surrounding the top of the aperture), the ratio of the penetration depth P the tapered length T (i.e., the dividend P/T) can be about 2 or less, about 1 or less, about 0.5 or less, or about 0.25 or less. The portion of the pin 20 that extends beyond the perimeter 41 of the female roll 42 and into the receiving recess 44 is the penetrating end 29 of the pin 20, which can have a taper that is nonlinear, such as the convex taper shown in the penetrating end 29 of the pin 20 in FIGS. 1A–1D, or a linear taper (not shown).

At mid-nip in an aperturing nip 35 (i.e., where the female roll 42 and the pin roll 50 are most proximate), the gap distance G is the span of the gap 43 between the perimeter 41 of the female roll 42 and the support surface 34 of the support 32 (generally part of the pin roll 50). The gap distance G can be equal to or greater than the thickness of the web (not shown) being apertured when compressed in the nip 35, and is the sum of the shaft length S and the exposed tapered section length X. The exposed tapered section length X is the length of the portion of the tapered section 26 that remains between the perimeter 41 of the female roll 42 and the support surface 34 on the pin roll 50; in other words, the exposed tapered section length X is the difference between the tapered length T and the penetration depth P.

Figure 1A:
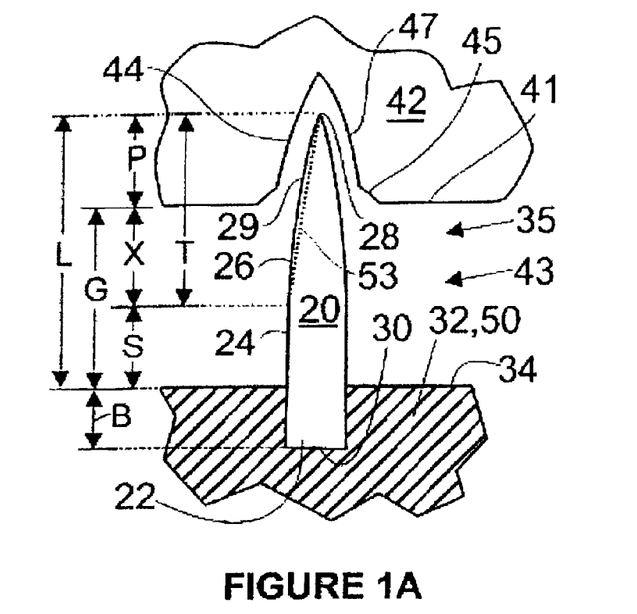
FIGS. 1A–1D show cross-sectional views of several embodiments of a pin of the present invention rising from a pin roll and extending in the receiving recess of a female roll.

Referring specifically to FIG. 1A, the receiving recess 44 in the female roll 42 can have a short chamfered section 45 which is broader than the rest of the receiving recess 44 (e.g., a flared lip at the outer portion of the receiving recess 44) to allow the tip 28 of the pin to avoid collision with the solid wall of the receiving recess 44 as the pin 20 rotates in and out the receiving recess 44. The chamfered section 45 may extend only in the machine direction (either toward the upstream or downstream side of the receiving recess 44 or on both sides as shown in FIG. 1A). The chamfered section 45 need not be axisymmetric about the centerline of the receiving recess 44. Moving into the receiving recess 44 away from the pin roll 50, an concave section 47 is encountered which is adapted to receive the tapered section 26 of the pin 20, resulting in significant densification of any portion of a web (not shown) present between the pin 20 and the wall of the concave section 47 of the receiving recess 44. In FIG. 1A, the receiving recess 44 is closed away from the perimeter 41.

FIG. 1A also shows a line 53 drawn from the tip 28 of the pin 20 to the top of the broadest portion of the exposed pin 20 in the gap 43 between the perimeter 41 of the female roll 42 and the support surface 34. The broadest portion of the exposed pin 20 in the gap 43 is the uppermost portion of the shaft 24, or, equivalently, the lower end of the tapered section 26. Because the tapered section 26 is substantially convex, the line 53 does not pass through air, but remains within the boundaries of the pin 20. When a pin 20 is substantially free of concave regions such that a line 53 from the tip 28 to the broadest portion of the pin 20 in the gap 43 remains within the pin 20, is said to be "macroscopically convex."

Figure 1B:
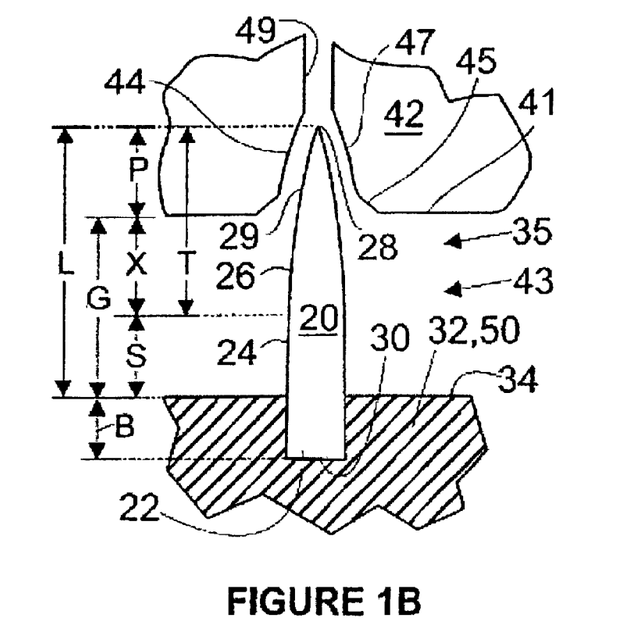

FIG. 1B is substantially identical to FIG. 1A except that the receiving recess 44 is open away from the perimeter 41 of the female roll 42, as the receiving recess 44 further comprises an open bore 49 distal to the perimeter 41 of the female roll 42. The open bore 49 can permit gas flow from an interior source to blow away debris or web fragments that might be dislodged from the web during aperturing, and can further permit heated or cooled gas to flow into the web during aperturing to further control material properties of the apertured portion of the web (not shown). For example, hot gas may be used to soften a thermoplastic film on either side of the web, or to soften binder fibers in the web near an aperture. In another embodiment, cold gas may be used to cool a section of a web apertured by a heated pin 20.

Figure 1C:
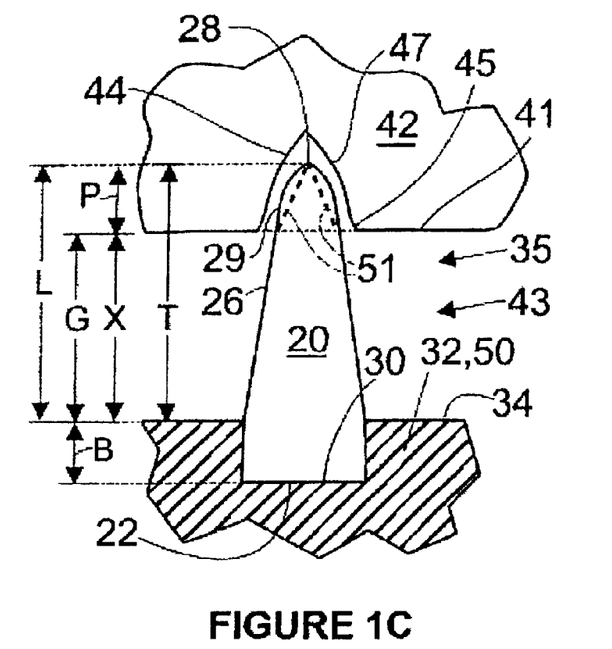

FIG. 1C shows a pin 20 having a tapered section 26 that essentially occupies the full extending length L of the pin 20 (L substantially equals T), and wherein the gap distance G substantially equals the exposed tapered section length X. The pin 20 has a substantially linear taper in the exposed portion of the tapered section 26 and a convex taper in the penetrating end 29 that extends into the receiving recess 44 of the female roll 42. If the entire tapered section 26 of the pin 20 had a linear taper, the overall shape of the displayed cross-section would be triangular, with straight lines extending from the portions of the pin immediately adjacent the support surface 34 to the tip 28 of the pin 20. With the convex shape of the top end of the pin 20 as shown, the overall taper of the tapered section 26 is nonlinear. The nonlinear taper—i.e., the convex shape of the pin—results in more of the volume of the receiving recess 44 being occupied by the end of the pin 20 in the receiving recess 44 than if the taper was linear. By way of example, a hypothetical linear end taper 51 is shown as dotted lines in the upper end of the pin 20 to illustrate a linear taper having the same width entering the receiving recess 44 as the nonlinearly tapered pin 20 illustrated in FIG. 1C. The hypothetical linear end taper 51 can clear the sides of the receiving recess 44 as it enters and leaves as well as the nonlinearly tapered pin 20 does, but it occupies less volume in the receiving recess 44 and leaves a larger distance between the sides of the pin 20 and the walls of the receiving recess 44, resulting in less compression of the web and poorer clarity or definition of the aperture. Thus, a nonlinear taper in the portion of the pin 20 that enters the receiving recess 44 contributes to improved aperturing. Further, an overall non-linear profile of the tapered section 26 of the pin 20 contributes to reduced friction and less displacement of the web in the aperturing nip, resulting in better aperturing and less disruption of the web. Thus, advantages can be obtained by an extended tapered section 26 (whether linear or nonlinear) that extends into the gap of the aperturing nip 35, as well as by a nonlinear convex taper in the portion of the pin 20 that extends into the receiving recess 44.

Figure 1D:
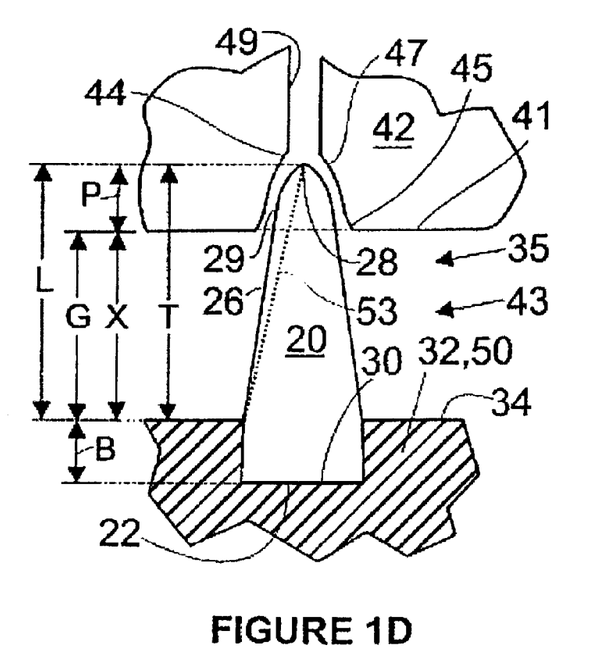

FIG. 1D has a pin 20 of shape substantially the same as in FIG. 1C, while the receiving recess 44 of FIG. 1D has an open bore 49 similar to that of FIG. 1B. The pin 20 of FIG.

1D is said to be macroscopically concave, for an imaginary line 53 drawn from the tip 28 of the pin (or, in cases where a tip is not well defined, from the center of the end of the pin 20) to the broadest portion of the pin 20 in the gap 43 does not cross any the boundaries of the pin 20, but remains within the pin 20.

Figure 2:
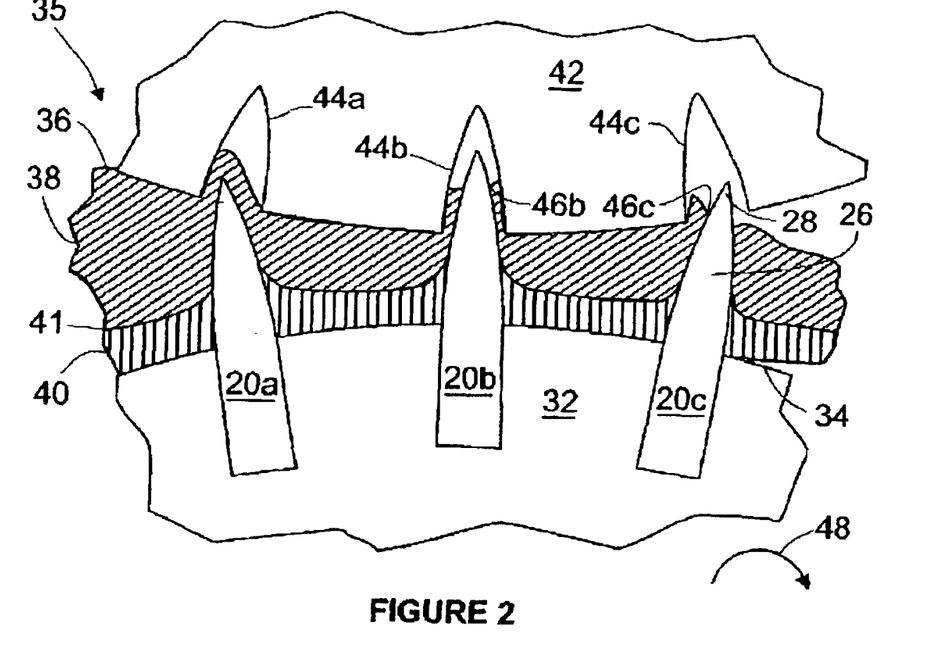
FIG. 2 is a cross-sectional view of an aperturing nip showing pins aperturing a composite web assembly.

FIG. 2 is a cross-sectional view of a portion of an aperturing nip 35 in which a composite web assembly 36 is coapertured between a pin roll 50 and a female roll 42. The pin roll 50 comprises a base roll 52 with a pin support 32 attached, which can be curved plates adapted to hold the pins 20a–20c.

The composite web assembly 36 comprises an absorbent layer 38 such as a cellulosic airlaid web or a fluff pulp mat formed from comminuted fibers superposed on a carrier layer 40 such as a nonwoven web or film that can serve as the liquid-pervious topsheet of an absorbent article (not shown). At the interface 41 between the carrier layer 40 and the absorbent layer 38, continuous or spaced apart adhesive (not shown) may be present to prevent slippage of the two layers 38, 40 relative to one another during aperturing, or other means such as a tissue layer (not shown) or pneumatically deposited fibers (not shown) may be present to improve contact or fluid communication between the two layers 38, 40.

The adhesive layer is desirably a thin, substantially continuous layer of adhesive and may desirably be a layer or system such as, for example, the adhesive layer or system described in U.S. patent application Ser. No. 60/336,096, entitled "Adhesive System For Mechanically Post-Treated Absorbent Structures" filed by Christine M. Cowell et al. assigned to the assignee of the present application and filed on even date herewith. The contents of that patent application are incorporated herein by reference in their entirety.

The carrier layer 40 can be a thin, flexible layer comprising synthetic polymer materials such as polyolefins, polyesters, nylon, and the like, and can be an extruded film, a cast film, a fabric, a meltblown web, a spunbond web, a bonded carded web, an electrospun web, a spunlace web, a coform web, and the like, or combinations thereof (e.g., films joined to fibrous nonwoven webs). Other exemplary nonwoven webs include those of U.S. Pat. No. 6,306,234, issued Oct. 23, 2001 to Barker et al., which discloses a nonwoven web with cross-directional extensibility and recovery.

The composite web assembly 36 can have various strata selected based upon the desired characteristics of the absorbent article into which it will be introduced. For example, the composite web assembly may have a preliminary liquid absorbent component that has an open top strata or layer that acts as a surge layer and helps prevent the flow back of liquid once it has been trapped and absorbed by the article. Additionally, the first liquid absorbent component desirably includes a transfer or wicking layer.

Many different types of coherent, flexible matrices including stratified layers of fibrous material may be used as the preliminary liquid absorbent component. Examples of suitable materials that are useful in the present invention include several multifunctional air laid materials available from Buckeye Technologies, Inc. (Memphis, Tenn.). One such material comprises an air-formed multi-strata web comprised of polyester (PET) fibers, fluff cellulose fibers and chemically modified cellulose fibers that are formed onto a carrier tissue sheet, which is then bonded with a combination of a PET/polyethylene bi-component binder fiber and an ethylvinyl alcohol-based latex emulsion.

Binders can be used to help provide mechanical integrity and stabilization. Binders include fiber, liquid or other binder means which may thermally activated. Desirable binder fibers include those having a relative melting point such as polyolefin fibers. Fibers having a lower melting polymer, like conjugate and biconstituent fibers are desirable. Fibers having a lower melting polymer are generally referred to as "fusible fibers". By "lower melting polymers" what is meant are those having a glass transition temperature less than about 175 C. It should be noted that the texture of the absorbent web could be modified from soft to stiff through selection of the glass transition temperature of the polymer. Exemplary binder fibers include conjugate fibers of polyolefins, polyamides and polyesters. Exemplary binder fibers include sheath core conjugate fibers available from KoSa Inc. (Charlotte, N.C.) under the designation T-255 (Merge 34821 A) and T-256 or Copolyester designation, though many suitable binder fibers are known to those skilled in the art, and are available by many manufacturers such as Chisso and Fibervisions LLC of Wilmington, Del. KoSa has developed a suitable co-polyester binder fiber as a sheath core application and is known by designation T254 (low melt CoPET). A suitable liquid binder is KYMENE® 557LX available from Hercules Co. of Wilmington, Del. Other suitable liquid binders include ethylene vinyl acetate emulsion polymers sold by National Starch and Chemical Company (Bridgewater, N.J.) under the tradename DUR-O-SET® ELITE® series (including ELITE® 33 and ELITE® 22). Air Products Polymers and Chemicals sells other suitable binder fibers under the name AIRFLEX®.

Synthetic fibers include those made from polyamides, polyesters, rayon, acrylics, superabsorbents, TENCEL® regenerated cellulose and any other suitable synthetic fibers known to those skilled in the art. Synthetic fibers may also include kosmotropes for product degradation.

Many polyolefins are available for fiber production, for example polyethylenes such as Dow Chemical's ASPUN® 6811A liner low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Many other polyolefins are also available.

Particularly preferred materials for this application include polyesters, which may range in size or denier from 3 to 25 denier, and having various cross-sections including round, pentalobal, helical crimped, etc. Such fibers have been, developed by KoSa, Inc. with a durably wettable finish and are known by designation of fiber denier followed by polymer type and cross section. Examples would include 8 dpf, T-224 (High Void); 8 dpf, T-224 (trilobal); 15 dpf T-224 (round); 10 dpf T-224 (round); 6 dpf T-224 (round) and 3 dpf T-224 (round).

Natural fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes, maleic anhydride, non-methylolated urea derivatives, citric acid or other polycarboxylic acids. Some of these agents are less preferable than others due to environmental and health concerns. Pulp may also be stiffened use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation. Suitable rayon fibers are 1.5 denier Merge 18453 fibers from Tencel Incorporated of Axis, Ala.

As a more detailed example, an exemplary material suitable for the first liquid absorbent component is available from Buckeye Technologies, Inc. under the trade designation Buckeye Unicore 8001. This air-formed or air-laid multi-strata material may have a total basis weight in the range from about 120 to about 300 (desirably between about 210 and 240) grams per square meter (gsm) and an overall density ranging from about 0.06 to about 0.10 grams per cubic centimeter (g/cm3). Exemplary multi-strata materials may have a top or uppermost layer of about 25 to about 45 gsm that contains latex bonded polyester fibers ranging from about 6 to about 15 denier per fiber (dpf) and which desirably make up about 20% of the total basis weight of the strata in the first liquid absorbent component. An immediately adjacent layer may be about 35 to about 70 gsm and may contain cellulose fiber joined with a binder fiber. The cellulose may be mercerized cellulose that is thermally bonded utilizing a bicomponent polyester/polyethylene binder fiber. This layer may desirably make up about 30% of the total basis weight of the strata. The multi-strata material may further include a layer that is about 35 to about 100 gsm and may include a compressible cellulose and binder fiber of the same or similar type as in the adjacent layer. This other layer may make up about 40% of the total basis weight of the strata. These layers may be formed on or supported by a carrier tissue that may range from about 10 to about 20 gsm and may desirably make about 5 percent of the total basis weight of the strata.

Other examples of suitable coherent, flexible matrices including stratified layers of fibrous material that may be used as the first liquid absorbent component can be found in International Publication Number WO 00/74620. According to that publication, the terms "strata" and "stratum" refer to the layered regions which make up a unitary structure. The strata of the unitary structure is not an assembly or laminate of preformed layers forming a multilayered structure. Instead, the unitary structure is constructed by assembling the strata in a continuous, manner. Airlaid technology is described as the method for assembling the strata of the unitary structure.

Another example of a suitable coherent, flexible matrix including stratified layers of fibrous material that may be used as the first liquid absorbent component has two strata or layers. The first layer is an air-laid structure having a basis weight of about 50 gsm and containing 85%, by weight, polyester fibers—15 denier per filament that is bonded together with about 15%, by weight, of a conventional latex binder suitable for personal care products. The second layer is an air-laid structure having a basis weight of about 150 gsm and containing about 90%, by weight, cellulose fluff and about 10%, by weight, bi-component binder fibers composed of a polyester core and a polyethylene or polyethylene-like sheath that softens or melts when heat is applied to dry the latex binder and thermally activate the binder fibers. This specific combination layers had an overall thickness of about 1.6 millimeters.

The pin roll 50 comprises pins 20a–20c in the partial section of the pin roll 50 shown. The pin have an extended tapered section 26 capable of being received in the receiving recesses 44a–44c, respectively, of the female roll 42. The pin roll 50 rotates in the clockwise direction 48 shown and the composite web assembly 36 moves from left to right in FIG. 2.

A pin 20a is shown as having punctured the carrier layer 40 but not yet the absorbent layer 38. An aperture 46b has been formed as the pin 20b has fully passed through the composite web assembly 36 with the tip 28 of the pin 20b extending beyond the absorbent layer 38 in the receiving recess 44b in the female roll 42. Another pin 20c has also formed an aperture 46c in the composite web assembly 36.

Figure 3:
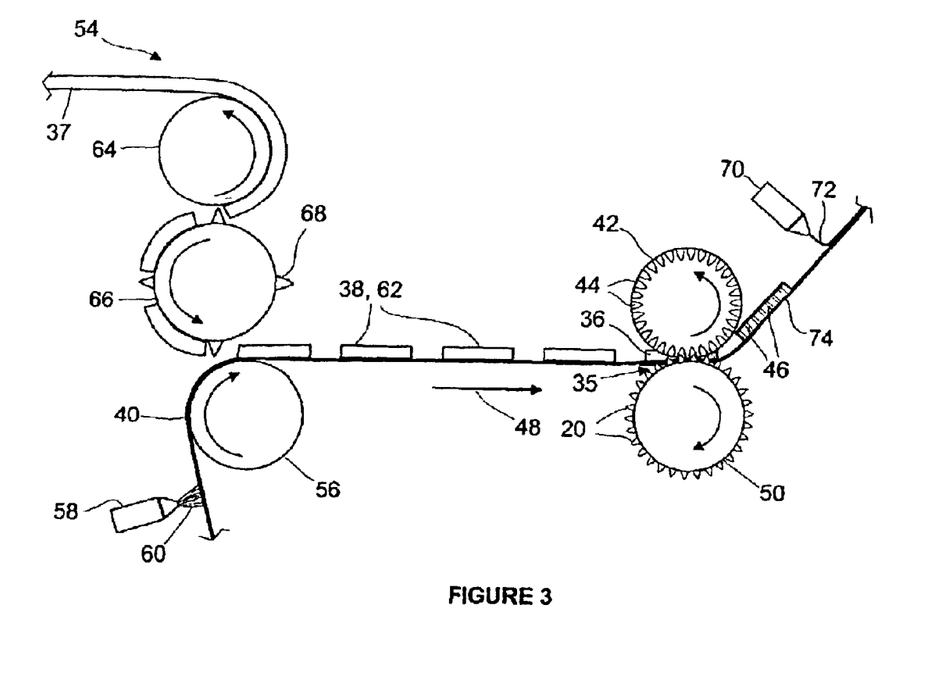
FIG. 3 depicts a portion of a machine for the manufacture of apertured absorbent articles according to the present invention.

FIG. 3 depicts a portion of a machine 54 for the manufacture of apertured absorbent articles according to the present invention. A fibrous absorbent web 37 such as a mat of fluff pulp, a coform layer, an airlaid web, a stack of absorbent tissue layers, or combinations thereof, is carried over a backing roll 64 opposed to a cutting roll 66 having spaced part cutting blades 66 thereon. The cutting roll 66 can be moving at a higher velocity than the backing roll 64 and the absorbent layer such that the cut sections 62 of the absorbent web 37 become spaced apart as they are subsequently deposited on a moving carrier layer 40 as it passes over a support roll 56 which can be a vacuum roll to assist transfer. Alternatively or in addition, transfer of the cut sections 62 and their attachment to the carrier layer 40 can be assisted by other known means (not shown) such as a vacuum box, air jets, mechanical arms, and the like. The moving carrier layer 40 can move at a higher speed than the fibrous absorbent web 37 and further can move at a higher speed than the cutting roll 66 to control the spacing of the cut sections 62 on the carrier layer 40, which generally moves in a machine direction 48. To improve the attachment of the cut sections 62 of the fibrous absorbent web 37 on the carrier layer 40, the carrier layer can be provided with suitable timed pulses of an adhesive spray 60 delivered by a first adhesive applicator 58. The cut sections 62 are absorbent layers 38 which, together with the carrier layer 40 and any other added materials (not shown), form sections of a composite web assembly 36 which enter an aperturing nip 35 between a lower pin roll 50 provided with a plurality of suitably tapered pins 20 and an upper female roll 42 provided with opposing receiving recesses 44. In-plane deformation of the composite web assembly 36 during aperturing is reduced by the presence of the adhesive delivered by the first adhesive applicator which reduces the tendency for the absorbent layer 38 to slide relative to the carrier layer 40 in the aperturing nip 35, and further by the tapered design of the pins 20 in contact with the composite web assembly 36.

The composite web assembly 36 after passing through the aperturing nip 35 is provided with apertures 46, thus becoming an apertured composite web assembly 74.

Clean withdrawal of the pins 20 from the composite web assembly 36 is aided by the wrap of the carrier layer 40 (and thus of the composite web assembly 36) as it leaves the nip 35, wherein the carrier layer 40 is wrapped around a portion of the female roll 42 before separating therefrom, which means that the composite web assembly 36 deflects upward at an angle relative to horizontal after the aperturing nip 35.

The upper surface of the carrier layer 40 is further provided with adhesive from a second adhesive applicator 70 which delivers one or more streams of adhesive 72 to the carrier layer 40, in preparation for attachment to a backsheet (not shown) or other components of an absorbent article (not shown). Typically, one or more adhesive streams 72 (either a fine flow of adhesive in liquid form or an oscillating stream or spray) are applied on the carrier layer 40 to the sides of the absorbent layer 38 for good bonding to a backsheet (not shown).

All rolls 42, 50, 56, 64, and 66 rotate as shown.

Figure 4:
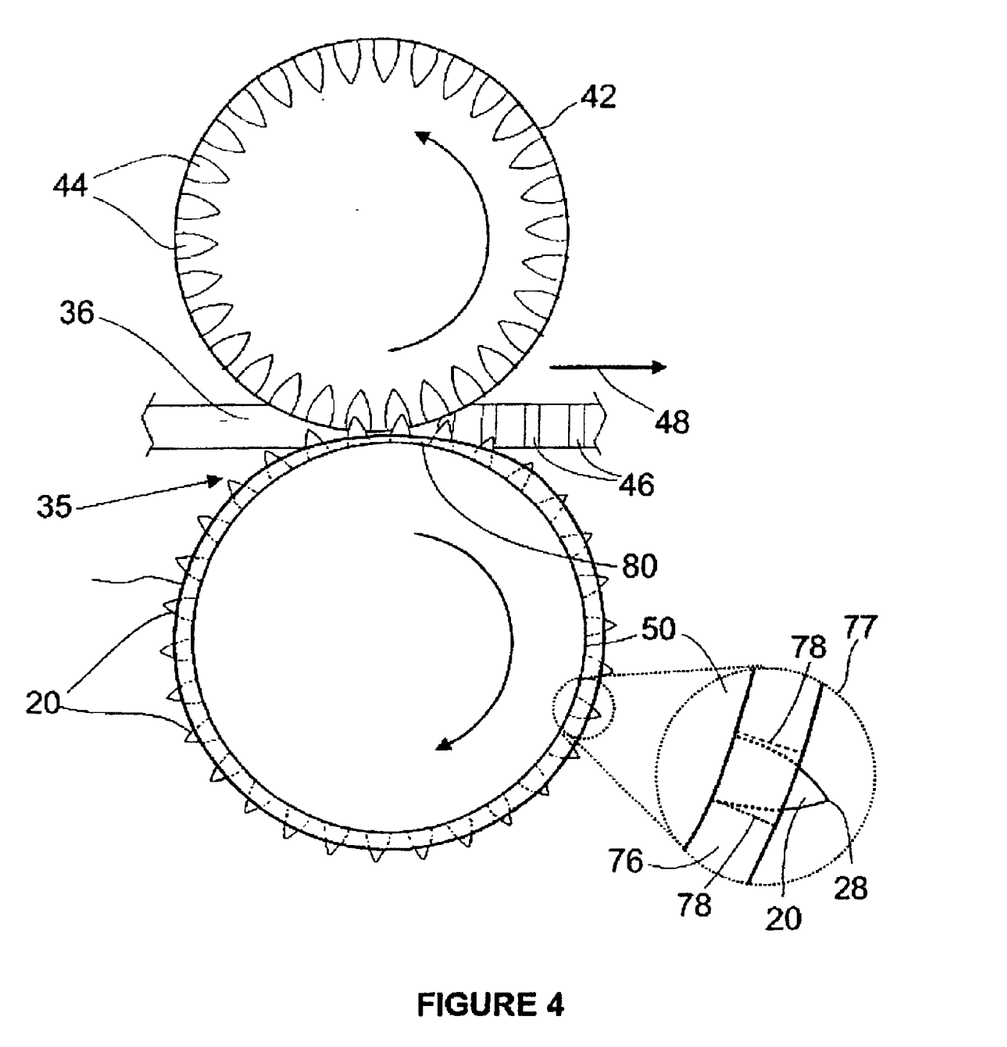
FIG. 4 is a schematic of an aperturing nip comprising a deformable restraint layer.

FIG. 4 depicts an embodiment to further reduce in-plane deformation during aperturing by means of a deformable restraint layer 76 disposed on the pin roll 50. The restraint layer 76 generally circumscribes the pin roll 50 and has wells 78 that are openings that receive the pins 20 of the pin roll 50. In the undeformed state (when there is no applied pressure), the thickness of the restraint layer 76 can be less than the length of the pins 20 above the pin roll 50, or the thickness can be equal to or greater than the length of the pins 20 above the pin roll 50. A magnified view 77 shows details of the well 78 that receives a pin 20, showing an embodiment in which the tip 28 of the pin 20 extends above the perimeter of the restraint layer 76.

In the aperturing nip 35, the restraint layer reduces the potential scope of in-plane deformation of the web 36 as it moves through the nip 35 in the machine direction 48. The restraint layer 76 becomes compressed in the aperturing nip 35, and a compressed section 80 is shown. The compressed section 80 provides a surface that can hold the web 36 in place and, in some embodiments, effectively grip the web 36 to reduce slipping relative to the surface of the pin roll 50 and shear relative to pins 20, thus further improving aperturing and the definition of the apertures 46 in the web 36.

FIG. 5 illustrates a prior art pin 20 taken from a figure of U.S. Pat. No. 5,188,625, issued Feb. 23, 1993 to Van Iten, et al., previously incorporated by reference. The Van Iten pin 20 has a broad pin base 94 wider than the receiving recess 44, providing a shoulder 96 from which an upper section 98 rises. The upper section 98 of the pin 20 is the penetrating portion of the pin 20, rising into the receiving recess 44 and creating an aperture 46 in the web 36. The receiving recess 44 is a straight closed bore with substantially vertical walls. The portion of the web 36 around the aperture 46 is in contact with an untapered region of the pin, having substantially vertical sides, though a slight concave taper exists at the rounded junction 97 of the upper section 98 and the pin base 94. Considering the overall shape of the pin 20 from the pin base 94 to the tip 28, the pin 20 is substantially devoid of convex tapering.

At the end of the pin 20 is a linear end bevel 99 which brings the pin 20 to a pointed tip 28. The end bevel 99 is shown to not in contact with the web 36 at this point. Since the portions of the pin 20 in contact with the web 36 are substantially untapered (i.e., the sides of the pin 20 are substantially vertical at mid nip), withdrawing the pin 20 can pose challenges due to high fraction. In addition to problems with in-plane deformation and difficulty in pin withdrawal that can be caused by the lack of taper in the web-contacting portions of the pin 20 at mid-nip, the high angle of short end bevel (here about 45° from vertical) can also cause the pin 20 to stamp out portions of the web 36 rather than creating clean apertures 46 without cut-out web fragments.

The Restraint Layer

The deformable restraint layer, if present, desirably contacts the web before it is engaged by the pins, and continues to contact and grip the web as the pins penetrate into the receiving recess of the female roll, preventing in-plane slippage. The deformable restraint layer may be any flexible cover material known in the art of papermaking (especially the art of soft calendering), including elastomers, and may comprise neoprene, deformable silicone materials, natural rubber, butyl rubber, buna-N (nitrile rubber), choroprene, ethylene-propylene-diene monomer rubber (EPDM rubber); chlorosulfonated polyethylene, fluoropolymers (e.g., copolymers of vinylidene fluoride and hexafluoropropylene), deformable silicone polymers and gels, polymeric foams, and the like. The deformable restraint layer may also comprise an outer film and an inner fluid such as a liquid or a gas.

Wells to receive the pins of the pin roll can be provided by any known means, including formation of the restraint layer in place over a pin roll, stamping or cutting holes in the restraint layer to match the pin pattern of a pin rill, laser drilling, laser ablation, contacting with heated elements to melt or burn holes in the restraint layer, and the like.

The Absorbent Layer

The fibrous web to be treated can be made by any method known in the art. Airlaid webs can be used, such as those made with DanWeb or Kroyer equipment. The web can be wetlaid, such as web formed with known papermaking techniques wherein a dilute aqueous fiber slurry is disposed on a moving wire to filter out the fibers and form an embryonic web which is subsequently dewatered by combinations of units including suction boxes, wet presses, dryer units, and the like. Examples of known dewatering and other operations are given in U.S. Pat. No. 5,656,132 to Farrington et al. Capillary dewatering can also be applied to remove water from the web, as disclosed in U.S. Pat. Nos. 5,598,643 issued Feb. 4, 1997 and 4,556,450 issued Dec. 3, 1985, both to S. C. Chuang et al.

Drying operations can include drum drying, through drying, steam drying such as superheated steam drying, displacement dewatering, Yankee drying, infrared drying, microwave drying, radiofrequency drying in general, and impulse drying, as disclosed in U.S. Pat. No. 5,353,521, issued Oct. 11, 1994 to Orloff; and U.S. Pat. No. 5,598,642, issued Feb. 4, 1997 to Orloff et al. Other drying technologies can be used, such as those described by R. James in "Squeezing More out of Pressing and Drying," *Pulp and Paper International*, Vol. 41, No. 12 (December 1999), pp. 13–17. Displacement dewatering is described by J. D. Lindsay, "Displacement Dewatering To Maintain Bulk," *Paperi Ja Puu*, vol. 74, No. 3, 1992, pp. 232–242. In drum drying, the dryer drum can also be a Hot Roll Press (HRP), as described by M. Foulger and J. Parisian in "New Developments in Hot Pressing," *Pulp and Paper Canada*, Vol. 101, No. 2, February, 2000, pp. 47–49. Other methods employing differential gas pressure include the use of air presses as disclosed U.S. Pat. No. 6,096,169, "Method for Making Low-Density Tissue with Reduced Energy Input," issued Aug. 1, 2000 to Hermans et al.; and U.S. Pat. No. 6,143,135, "Air Press For Dewatering A Wet Web," issued Nov. 7, 2000 to Hada et al. Also relevant are the paper machines disclosed in U.S. Pat. No. 5,230,776 issued Jul. 27, 1993 to I. A. Andersson et al.

A moist fibrous web can also be formed by foam forming processes, wherein the fibers are entrained or suspended in a foam prior to dewatering, or wherein foam is applied to an embryonic web prior to dewatering or drying. Exemplary methods include those of U.S. Pat. No. 5,178,729, issued Jan. 12, 1993 to Janda; and U.S. Pat. No. 6,103,060, issued Aug. 15, 2000 to Munerelle et al., both of which are herein incorporated by reference.

For tissue webs, both creped and uncreped methods of manufacture can be used. Uncreped tissue production is disclosed in U.S. Pat. No. 5,772,845 to Farrington, Jr. et al., herein incorporated by reference. Creped tissue production is disclosed in U.S. Pat. No. 5,637,194 to Ampulski et al., U.S. Pat. No. 4,529,480 to Trokhan, U.S. Pat. No. 6,103,063, issued Aug. 15, 2000 to Oriaran et al., and U.S. Pat. No. 4,440,597 to Wells et al, all of which are herein incorporated by reference in a manner consistent herewith.

For either creped or uncreped methods, embryonic tissue webs may be imprinted against a deflection member prior to complete drying. Deflection members have deflection conduits between raised elements, and the web is deflected into the deflection member by an air pressure differential to create bulky domes, while the portions of the web residing on the surface of the raised elements can be pressed against the dryer surface to create a network of pattern densified areas offering strength. Deflection members and fabrics of use in imprinting a tissue, as well as related methods of tissue manufacture, are disclosed in the following: in U.S. Pat. No. 5,855,739, issued to Ampulski et al. Jan. 5, 1999; U.S. Pat. No. 5,897,745, issued to Ampulski et al. Apr. 27, 1999; U.S. Pat. No. 4,529,480, issued Jul. 16, 1985 to Trokhan; U.S. Pat. No. 4,514,345, issued Apr. 30, 1985 to Johnson et al.; U.S. Pat. No. 4,528,239, issued Jul. 9, 1985 to Trokhan; U.S. Pat. No. 5,098,522, issued Mar. 24, 1992; U.S. Pat. No. 5,260,171, issued Nov. 9, 1993 to Smurkoski et al.; U.S. Pat. No. 5,275,700, issued Jan. 4, 1994 to Trokhan; U.S. Pat. No. 5,328,565, issued Jul. 12, 1994 to Rasch et al.; U.S. Pat. No. 5,334,289, issued Aug. 2, 1994 to Trokhan et al.; U.S. Pat. No. 5,431,786, issued Jul. 11, 1995 to Rasch et al.; U.S. Pat. No. 5,496,624, issued Mar. 5, 1996 to Stelljes, Jr. et al.; U.S. Pat. No. 5,500,277, issued Mar. 19, 1996 to Trokhan et al.; U.S. Pat. No. 5,514,523, issued May 7, 1996 to Trokhan et al.; U.S. Pat. No. 5,554,467, issued Sep. 10, 1996, to Trokhan et al.; U.S. Pat. No. 5,566,724, issued Oct. 22, 1996 to Trokhan et al.; U.S. Pat. No. 5,624,790, issued Apr. 29, 1997 to Trokhan et al.; U.S. Pat. No. 6,010,598, issued Jan. 4, 2000 to Boutilier et al.; and U.S. Pat. No. 5,628,876, issued May 13, 1997 to Ayers et al., as well as commonly owned application Ser. No. 09/705,684 by Lindsay et al., all of which are herein incorporated by reference in a manner consistent herewith.

The fibrous web is generally a random plurality of papermaking fibers that can, optionally, be joined together with a binder. Any papermaking fibers, as previously defined, or mixtures thereof may be used, such as bleached fibers from a kraft or sulfite chemical pulping process. Recycled fibers can also be used, as can cotton linters or papermaking fibers comprising cotton. Both high-yield and low-yield fibers can be used. In one embodiment, the fibers may be predominantly hardwood, such as at least 50% hardwood or about 60% hardwood or great or about 80% hardwood or greater or substantially 100% hardwood. In another embodiment, the web is predominantly softwood, such as at least about 50% softwood or at least about 80% softwood, or about 100% softwood.

For many tissue applications, high brightness may be desired. Thus the papermaking fibers or the resulting paper of the present invention can have an ISO brightness of about 60 percent or greater, more specifically about 80 percent or greater, more specifically about 85 percent or greater, more specifically from about 75 percent to about 90 percent, more specifically from about 80 percent to about 90 percent, and more specifically still from about 83 percent to about 88 percent.

The fibrous web of the present invention may be formed from a single layer or multiple layers. Both strength and softness are often achieved through layered tissues, such as those produced from stratified headboxes wherein at least one layer delivered by the headbox comprises softwood fibers while another layer comprises hardwood or other fiber types. Layered structures produced by any means known in the art are within the scope of the present invention, including those disclosed by Edwards et al. in U.S. Pat. No. 5,494,554. In the case of multiple layers, the layers are generally positioned in a juxtaposed or surface-to-surface relationship and all or a portion of the layers may be bound to adjacent layers. The paper web may also be formed from a plurality of separate paper webs wherein the separate paper webs may be formed from single or multiple layers.

Dry airlaid webs can also be treated with PVAm polymers. Airlaid webs can be formed by any method known in the art, and generally comprise entraining fiberized or comminuted cellulosic fibers in an air stream and depositing the fibers to form a mat. The mat may then be calendered or compressed, before or after chemical treatment using known techniques, including those of U.S. Pat. No. 5,948,507 to Chen et al., herein incorporated by reference.

Whether airlaid, wetlaid, or formed by other means, the web can be substantially free of latex and substantially free of film-forming compounds. The applied solution or slurry comprising PVAm polymers and/or the second compound can also be free of formaldehyde or cross-linking agents that evolve formaldehyde.

In one embodiment, the web being apertured comprises two layers differing in surface energy. The base of the aperture can then have a region where the uppermost material comes to an end but some of the lower material can surround the aperture and provide a surface energy gradient around the aperture (near the region where the pin broke through the cloth). If the lower layer is more strongly attracted to the fluid in question than the upper layer, then it can draw fluid effectively into the apertured region, from where the fluid can be absorbed in conventional ways. With the restraint offered by the surrounding deformable layer, the pin is less likely to pull the aperture hold up out of the plane or to cause discomfort because of the apertures in the film.

The Carrier Layer

The carrier layer, if present in the web or composite web assembly being apertured, can be any liquid cover material known in the art for absorbent articles, such as covers used in contact with the body for receiving urine, menses, or other body fluids. Cover materials can include spunbond webs, meltblown webs, apertured films, tissue-nonwoven composites, elastomeric webs, and the like. Covers can be made from any polymer or other material known in the art, such as polyolefins, polyesters, nylon, polyamides, as well as from cotton, tissue, or other cellulosic materials or other natural fibers. Other useful cover materials are disclosed in U.S. Pat. No. 5,990,377, "Dual-Zoned Absorbent Webs," issued Nov. 23, 1999 to Chen et al.

Thermal Treatments

In many embodiments, it is desirable to combine heating of the web or parts of the web with the aperturing process to improve the definition of the apertures, to modify the densification of the web, to adjust the mechanical properties of the web, or for other purposes. The web can be heated conductively, such as by using heated pins in the aperturing nip which can soften the material being apertured and fuse binder material in the vicinity of the aperture for better stability and definition of the aperture. The female roll can also be heated, and both the pin roll and the female roll can be heated, if desired. Alternatively or in combination with heating in the aperturing nip, the web can be heated prior to entry into the aperturing nip. Preheating can be achieved conductively, as by contacting the web to a heated roll, passing the web through a flow of heated air or steam, applying microwave or other radiofrequency energy, induction heating of electrically conductive elements in the web, applying infrared radiation, applying ultrasonic energy, and the like. One form of convective heat transfer of value in the present invention is the hot air knife, or HAK, as described in U.S. Pat. No. 5,962,112, issued Oct. 5, 1999 to Haynes et al., herein incorporated by reference.

Rolls and pins can be heated by any known method, such as by externally applied infrared radiation or gas flame, induction heating, or by internal heating from a flow of steam, hot oil or other heat transfer fluid, or by the use of combustion inside the roll (e.g., an internal natural gas flame).

In one embodiment, the pins or other portion of the aperturing nip conveys ultrasonic energy from a rotating ultrasonic horn to the web to cause local heating.

Radiofrequency Treatment

The use of radiofrequency energy, microwaves or other electromagnetic means of applying energy to a web can allow more uniform treatment of the web or of any binder material in the web. As used herein, "radiofrequency" (RF) energy comprises electromagnetic radiation in the spectral range of 300 Hz to 300 GHz. "Microwave radiation" is a subset of RF radiation spanning the spectral range from 30 MHz to 300 GHz. Typical frequencies for microwave energy are 915 MHz and 2450 MHz (2.45 GHz), the ISM bands allowed by the Federal Communication Commission (FCC). General principles for microwave heating are given by R. C. Metaxas and R. J. Meredith in *Industrial Microwave Heating*, Peter Peregrinus, LTD, London, 1983. A useful tool in the design of microwave heating systems is the HFSS™ software provided by Ansoft Corp. (Pittsburgh, Pa.).

When radiofrequency energy is applied, the web can incorporate binder materials such as thermoplastic binder fibers or curable resins that are relatively sensitive to radiofrequency radiation (compared to pure cellulose itself) by virtue of a high dipole moment. In one embodiment, microwave energy is applied to the moving web as it passes through an opening in a microwave resonance chamber, where microwave energy is focused into the web.

In one embodiment, applying sufficient energy to the absorbent web comprises application of microwaves to cause components in the web to heat sufficiently to fuse or melt thermoplastic binder materials without substantial fusing of any adjacent nonwoven layers such as a spunbond web. For example, an airlaid web can comprise fibers and/or particles of dipolar polymers such as polyurethanes, isocyanates, polyethylene oxide, polyester, and their derivatives, or mixtures or copolymers formed therefrom. Application of microwave radiation causes the dipolar polymers to become heated enough to either fuse or to cause other less dipolar thermoplastic materials to fuse. For example, a sheath-core bicomponent fiber with a polyester core and a polyolefin sheath can be subjected to microwave radiation to cause the core to heat sufficiently to cause melting of the sheath without melting or degradation of the core. Alternatively, the sheath can be more microwave susceptible than the core. An exemplary application of microwave energy is found in the commonly owned PCT publication WO 99/22686, "Composite Material with Elasticized Portions and a Method of Making the Same," by R. G. Brandon, F. M. Chen, and R. E. Vogt, U.S. Pat. No. 5,916,203, issued Jun. 29, 1999. Further details of providing microwave chambers for applying energy to a moving web are disclosed in U.S. Pat. No. 5,536,921, issued Jul. 16, 1996 to Hedrick et al.; U.S. Pat. No. 6,020,580; and U.S. Pat. No. 4,234,775, issued Nov. 18, 1980 to Wolfberg et al.; all of which are herein incorporated by reference.

U.S. Pat. No. 5,958,275, issued Sep. 28, 1999 to Joines et al., herein incorporated by reference, provides several useful embodiments for application of microwave energy to a moving planar material such as a web. The web passes through a slot in a microwave chamber that has adjustably variable path lengths to allow peaks and valleys of the electromagnetic field in one exposure segment to compensate for peaks and valleys in another exposure segment. For example, the microwave chamber may have a serpentine shape that makes several passes over the web to ensure uniform application of microwave energy. Specialized choke flanges prevent the escape of electromagnetic energy. One or more rollers between exposure segments in the microwave chamber may be enclosed by an outer surface to prevent the escape of electromagnetic energy.

In an embodiment related to the equipment disclosed in commonly owned U.S. application Ser. No. 09/603,714 by R. E. Vogt, filed Jun. 27, 2000, herein incorporated by reference, microwave energy is directed by a waveguide into a resonance chamber adapted to focus energy into a plane or along a line through which the moving web passes. A cylindrical chamber can be suitable, for example, wherein the web travels along a diameter of the chamber, entering and leaving through slots along opposing sides of the cylinder. Quarter-wavelength chokes extend outward from the slots to prevent excess leakage of microwave radiation through the slots. When tuned for microwave energy to fill the chamber in the $TM_{010}$ mode, the energy is focussed along the axis of the cylinder and thus into the web for efficient delivery of energy. (TM modes are generally expected to be useful for microwave heating of a web in the present invention. TEM modes can be used but are more likely to permit leakage of microwaves from the chamber.) The web may be carried on a belt of material such as Teflon™ that is relatively unsusceptible to microwave energy, or the web can pass through the chamber without being on a carrier belt.

General principles for use of cylindrical resonance chambers for microwave heating and the coupling of a waveguide to an aperture in the cylinder are given by R. C. Metaxas and R. J. Meredith in *Industrial Microwave Heating*, Peter Peregrinus, LTD, London, 1983, pp. 183–195. In general, a rectangular waveguide is choked down through an aperture in the center of the cylinder (e.g., on the top or bottom of the central portion of the cylinder when a web runs through the middle of the cylinder along the horizontal diameter) to provide efficient transfer and distribution of microwave energy into the cylinder.

U.S. Pat. No. 6,020,580, issued Feb. 1, 2000 to Lewis et al., herein incorporated by reference, discloses a suitable microwave applicator with an elongated chamber such as a cylindrical shape which can be used or adapted in accordance with Vogt (U.S. application Ser. No. 09/603,714) for use in the present invention. A waveguide, connected to the elongated chamber, couples microwave power into the elongated chamber. The cross-sectional area of the elongated chamber can be mechanically adjusted to control and maintain the microwave field uniformity and resonant mode, suitably a length independent mode $TM_{010}$, during the processing of the material. The applicator thus provides microwave energy having a substantially uniform field distribution over a large area for processing a web.

In addition to heating and activating thermoplastic binder materials, electromagnetic radiation in the form of microwaves or ultraviolet radiation, for example, can also be used to cure resins that are in liquid form. For example, an airlaid web or fluff web can be impregnated or sprayed with a liquid binder system, followed by application of light pressure to mold the web into a three-dimensional shape as radiation is applied to cure the liquid binder. Heat can also be applied to cure some binder systems, wherein the heat is applied by through drying or other convective means with hot gas passing into the web, infrared radiation, conduction, and the like. Examples of microwave and UV curing of resins in a fibrous preform is found in U.S. Pat. No. 5,169,571, issued Dec. 8, 1992 to D. T. Buckley, and in U.S. Pat. No. 5,338,169, issued Aug. 16, 1994, also to Buckley, both of which are herein incorporated by reference.

A method for simultaneously applying microwave radiation and applying moderate pressure to the web can be achieved by using a microwave-transparent solid material, or microwave window, as one of the surfaces pressing against a bulky web. Suitable microwave windows and cooling systems for the windows are disclosed in U.S. Pat. No. 5,228,947, "Microwave Curing System," issued Jul. 20, 1993 to M. T. Churchland, herein incorporated by reference in its entirety.

While the above examples typically are directed toward a web passing through stationary microwave equipment, the microwave energy or other energy sources for heating the web can be mounted to a moving structure (or energy from a stationary source can be guided into and distributed from a rotating device), such as a rotating wheel, or an moving belt or track, to move with the web for a predetermined length or time.

Other Embodiments

The pins may be treated with a lubricant to decrease friction with the web being apertured. Such lubricants can include any known wax, oil, emollient, mineral oil, glycerin, water, and the like.

In another embodiment, the pins are treated with a hydrophilic material to increase transport of fluid through the composite web assembly and particularly through the carrier layer, which may be hydrophobic. Such hydrophilic materials can include a polyol, a protein, a surfactant, starch, a polysaccharide solution, and the like. A liquid hydrophilic material such as a surfactant may also serve as a lubricant for reducing friction. Means for applying materials to pin and means for delivery materials from a pin to the web are disclosed in U.S. Pat. No. 4,820,294, issued Apr. 11, 1989 to Morris, herein incorporated by reference.

In another embodiment, the web can be stretched in the machine direction or cross-direction prior to entering the aperturing nip, while maintaining the stretching tension as the web is being apertured, after which the apertured web can be relaxed, as disclosed in U.S. Pat. No. 5,573,719, "Process of Making Highly Absorbent Nonwoven Fabric," issued Nov. 12, 1996 to Fitting. This process desirably is performed at a temperature below the softening point of the web. Such as process can impart additional stretch and texture to a web.

Definitions and Test Methods

As used herein, a material is said to be "absorbent" if it can retain an amount of water equal to at least 100% of its dry weight as measured by the test for Intrinsic Absorbent Capacity given below (i.e., the material has an Intrinsic Absorbent Capacity of at about 1 or greater). For example, the absorbent materials used in the absorbent members of the present invention can have an Intrinsic Absorbent Capacity of about 2 or greater, more specifically about 4 or greater, more specifically still about 7 or greater, and more specifically still about 10 or greater, with exemplary ranges of from about 3 to about 30 or from about 4 to about 25 or from about 12 to about 40.

As used herein, "Absorption Capacity" is a measure of the mass of water that a pad can hold after it has been immersed and withdrawn from a pool of water. Absorption Capacity is measured by immersing a clean dry pad in deionized water at 25° C. for 30 seconds, holding the pad in a flat, horizontal position with the primary working surface of the pad down, such that the highest portion of the pad is 3 inches below the surface of the water. The pad is then slowly withdrawn over a period of about 2 seconds and held without compression while still in a horizontal position to allow it to drip for 30 seconds, after which the pad is weighed. The gain in mass relative to the mass of the dry pad before immersion, divided by the mass of the dry pad, is the Absorption Capacity. The pad can have a water Absorption Capacity of at least any of the following: 4, 6, 8, 9, and 10, with exemplary ranges of from about 5 to about 10, or from about 6 to about 15.

As used herein, "Intrinsic Absorbent Capacity" refers to the amount of water that a saturated sample can hold relative to the dry weight of the sample and is reported as a dimensionless number (mass divided by mass). The test is performed according to Federal Government Specification UU-T-595b. It is made by cutting a 10.16 cm long by 10.16 cm wide (4 inch long by 4 inch wide) test sample, weighing it, and then saturating it with water for three minutes by soaking. The sample is then removed from the water and hung by one corner for 30 seconds to allow excess water to be drained off. The sample is then re-weighed, and the difference between the wet and dry weights is the water pickup of the sample expressed in grams per 10.16 cm long by 10.16 cm wide sample. The Intrinsic Absorbent Capacity value is obtained by dividing the total water pick-up by the dry weight of the sample. If the material lacks adequate integrity when wet to perform the test without sample disintegration, the test method may be modified to provide improved integrity to the sample without substantially modifying its absorbent properties. Specifically, the material may be reinforced with up to 6 lines of hot melt adhesive having a diameter of about 1 mm applied to the outer surface of the article to encircle the material with a water-resistant band. The hot melt should be applied to avoid penetration of the adhesive into the body of the material being tested. The corner on which the sample is hung in particular should be reinforced with external hot melt adhesive to increase integrity if the untreated sample cannot be hung for 30 seconds when wet.

"Papermaking fibers," as used herein, include all known cellulosic fibers or fiber mixes comprising cellulosic fibers. Fibers suitable for making the webs of this invention comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, and aspen. Woody fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628, issued Jan. 21, 1997 to Gordon et al. A portion of the fibers, such as up to 50% or less by dry weight, or from about 5% to about 30% by dry weight, can be synthetic fibers such as rayon, polyolefin fibers, polyester fibers, bicomponent sheath-core fibers, and the like. An exemplary polyethylene fiber is Pulpex®, available from Hercules, Inc. (Wilmington, Del.). Any known bleaching method can be used. Synthetic cellulose fiber types include rayon in all its varieties and other fibers derived from viscose or chemically modified cellulose. Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin. Characteristic high-yield fibers can have lignin content by mass of about 1% or greater, more specifically about 3% or greater, and still more specifically from about 2% to about 25%. Likewise, high yield fibers can have a kappa number greater than 20, for example. In one embodiment, the high-yield fibers are predominately softwood, such as northern softwood or, more specifically, northern softwood BCTMP.

As used herein, the term "cellulosic" is meant to include any material having cellulose as a major constituent, and specifically comprising about 50 percent or more by weight of cellulose or cellulose derivatives. Thus, the term includes cotton, typical wood pulps, nonwoody cellulosic fibers, cellulose acetate, cellulose triacetate, rayon, viscose fibers, thermomechanical wood pulp, chemical wood pulp, debonded chemical wood pulp, lyocell and other fibers formed from solutions of cellulose in NMMO, milkweed, or bacterial cellulose. lyocell, and can be viscose, rayon, and the like. Fibers that have not been spun or regenerated from solution can be used exclusively, if desired, or at least about 80% of the web can be free of spun fibers or fibers generated from a cellulose solution.

As used herein, the "wet:dry ratio" is the ratio of the geometric mean wet tensile strength divided by the geometric mean dry tensile strength. Geometric mean tensile strength (GMT) is the square root of the product of the machine direction tensile strength and the cross-machine direction tensile strength of the web. Unless otherwise indicated, the term "tensile strength" means "geometric mean tensile strength." The absorbent webs used in the present invention can have a wet:dry ratio of about 0.1 or greater and more specifically about 0.2 or greater. Tensile strength can be measured using an Instron tensile tester using a 3-inch jaw width (sample width), a jaw span of 2 inches (gauge length), and a crosshead speed of 25.4 centimeters per minute after maintaining the sample under TAPPI conditions for 4 hours before testing. The absorbent webs of the present invention can have a minimum absolute ratio of dry tensile strength to basis weight of about 0.01 gram/gsm, specifically about 0.05 grams/gsm, more specifically about 0.2 grams/gsm, more specifically still about 1 gram/gsm and most specifically from about 2 grams/gsm to about 50 grams/gsm.

As used herein, the term "polymeric web" refers to a porous or nonporous layer primarily composed of polymeric material, and can be a nonwoven web, a plastic film, a polymeric film, an apertured film, or a layer of foam. Polymeric webs can be used as wicking barriers, baffle layers, backsheets, and, if sufficiently liquid pervious, as topsheets of absorbent articles. A polymeric web can consist of about 50 weight percent or more polymeric material, more specifically about 80 weight percent or more polymeric material, and most specifically about 90 weight percent or more polymeric material. Exemplary materials include polyolefins, polyesters, polyvinyl compounds, and polyamides.

As used herein, "bulk" and "density," unless otherwise specified, are based on an oven-dry mass of a sample and a thickness measurement made at a load of 0.34 kPa (0.05psi) with a 7.62-cm (three-inch) diameter circular platen.

As used herein, the term "hydrophobic" refers to a material having a contact angle of water in air of at least 90 degrees. In contrast, as used herein, the term "hydrophilic" refers to a material having a contact angle of water in air of less than 90 degrees.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

We claim:

1. An aperturing device for aperturing a web having at least one cellulosic absorbent layer, comprising a pin roll having a surface with a plurality of tapered pins rising therefrom, an opposing female roll having a perimeter and comprising a plurality of receiving recesses adapted to receive the pins of the pin roll, wherein the pin roll and female roll are spaced apart and cooperatively associated to define a nip therebetween having a mid nip region with a mid-nip gap of finite gap width between the surface of the pin roll and the perimeter of the female roll, wherein the pins of the pin roll extend into the receiving recesses of the female roll in the aperturing nip, and the pins have a height above the surface of the pin roll and comprise a tapered section that has a length greater than the length of the section of the pin that extends into the receiving recess in the mid-nip region.

2. The device of claim 1, wherein the length of the tapered section of the pins is about 50% or greater of the height of the pins.

3. The device of claim 1, wherein the length of the tapered section of the pins is about 70% or greater of the height of the pins.

4. The device of claim 1, wherein the tapered section of the pins is substantially convexly tapered.

5. The device of claim 4, wherein the receiving recesses of the female roll comprises a concave section.

6. The device of claim 1 or 4, wherein the receiving recesses of the female roll comprises a concave section and an open bore.

7. The device claim 4, wherein the pin is convexly tapered such that a line extending from the tip of the pin to the broadest portion of the pin in the gap remains within the pin.

8. The device of claim 1, wherein the pins are heated.

9. The device of claim 1, wherein the receiving recesses of the female roll are provided with a chamfered section.

10. An aperturing device comprising a pin roll having a support surface with rigid pins extending therefrom, an opposing female roll having an outer surface and comprising receiving recesses adapted to receive the pins of the pin roll, the outer surface of the female roll being spaced apart from the support surface of the pin roll by a fixed gap distance to define an aperturing nip therebetween with a mid-nip region, wherein pins from the pin roll extend a penetration depth into the receiving recesses in the mid-nip region, wherein the pins are provided with a curved convex taper over a length at least as great as the penetration depth.

11. The device of claim 10, wherein the pins extend at least 2 mm above the support surface of the pin roll.

12. The device of claim 10, wherein the pins have a maximum diameter of at least 2 mm.

13. The device of claim 10, wherein the receiving recesses of the female roll are provided with a chamfered section.

14. An aperturing device comprising a pin roll having a support surface with rigid pins extending therefrom, an opposing female roll having an outer surface and comprising receiving recesses adapted to receive the pins of the pin roll, the outer surface of the female roll being spaced apart from the support surface of the pin roll by a fixed gap distance to define an aperturing nip therebetween with a mid-nip region, wherein pins from the pin roll extend a penetration depth into the receiving recesses in the mid-nip region, and wherein at least a portion of the support surface of the pin roll is covered with a deformable restraint layer.

15. The device of claim 14, wherein the pins comprise a tapered section having a convex taper across a tapered section length at least as great as the penetration depth of the pins in the receiving recesses at mid-nip.

16. An aperturing device for aperturing a web having at least one cellulosic absorbent layer, comprising a pin plate having a surface with a plurality of tapered pins rising therefrom, an opposing female plate having a surface and comprising a plurality of receiving recesses adapted to receive the pins of the pin plate, wherein at least one of the pin plate and female plate can be reciprocally moved to repeatedly bring the plates together to cause pins to enter the receiving recesses, wherein the pins have a height above the surface of the pin plate and comprise a tapered section that has a length greater than the maximum length of the section of the pin that extends into the receiving recess of the female plate.

17. A method of coaperturing a carrier layer and a hydrophilic absorbent layer, comprising:

a) joining the carrier layer and absorbent layer to form a composite web assembly;

b) providing an aperturing nip between a pin roll having a support surface and comprising rigid pins extending from the support surface and a female roll having an outer surface and comprising receiving recesses adapted to receive pins from the pin roll in the aperturing nip, the pins having a substantially convex tapered section at least as long as the maximum distance that the pins penetrate into the receiving recesses of the female roll in the aperturing nip; and c) passing the composite web assembly through the aperturing nip, wherein pins from the pin roll extend into the receiving recesses of the female roll and thereby form apertures in the composite web assembly.

18. The method of claim 17, further comprising heating at least one of the pins and the female roll.

19. The method of claim 17, further comprising providing the pin roll with a deformable restraint layer having wells therein to receive the pins.

20. The method of claim 17, further comprising wrapping the composite web assembly along a portion of the female roll after the composite web assembly exits from the aperturing nip.

21. A system for aperturing at least one layer of material comprising, a pin having a first and second end portions and a length extending between the end portions and an independent cooperating receiving recess; where the pin further comprises, a base on the first end of the pin, a tip on the second end of the pin, and a tapered portion that extends for some portion of the length of the pin, between the tip and the base, and where the independent cooperating receiving recess further comprises an opening, an empty recess and walls that extend from the opening and define the size and shape of the empty recess and is cooperatively shaped relative to the pin so that the pin can be extended through the opening into the empty recess while maintaining a gap between the pin and the walls;

the pin and independent cooperating receiving recess being designed and positioned relative to each other to interact with each other when at least one layer of material between them such that the tip of the pin minimally deflects the material, then the tip and a portion of the tapered portion of the pin pass through the material into the cooperating receiving recess, then the material is compressed between the receiving recess and the tapered portion of the pin, and then the pin is removed from the material.

22. The system of claim 21 where the tapered portion of the pin is convex in shape.

23. The system of claim 21 where the walls of the cooperating receiving recess are concave in shape.

24. The system of claim 21 where the receiving recess has an open bore distal to the opening of the receiving recess.

25. The system of claim 21 where at least either of the pin or the receiving recess is heated.

26. The system of claim 21 where the tapered portion of the pin simultaneously extends outside and inside of the cooperating receiving recess when the material is being compressed between the receiving recess and the tapered portion of the pin.

* * * * *